United States Patent  (10) Patent No.: US 7,622,511 B1
Sirdesai et al.  (45) Date of Patent: Nov. 24, 2009

(54) METHOD OF OBTAINING A TACK-FREE ARTIFICIAL NAIL SURFACE USING ODORLESS MONOMERS

(75) Inventors: Sunil J. Sirdesai, Irvine, CA (US); Lauren M. Breese, Santa Barbara, CA (US); George W. Schaeffer, Beverly Hills, CA (US)

(73) Assignee: OPI Products, Inc., North Hollywood, CA (US)

( * ) Notice: Subject to any disclaimer, the term of this patent is extended or adjusted under 35 U.S.C. 154(b) by 606 days.

(21) Appl. No.: 11/217,053

(22) Filed: Aug. 30, 2005

(51) Int. Cl.
*C08J 3/28* (2006.01)
*C08F 2/46* (2006.01)
*A61K 8/00* (2006.01)
*A61K 8/18* (2006.01)
*A61K 8/37* (2006.01)

(52) U.S. Cl. ........................ 523/105; 523/137; 523/300; 522/104; 522/107; 522/113; 522/114; 522/120; 522/121; 522/178; 522/182; 522/902; 424/61; 424/401

(58) Field of Classification Search ................. 424/401, 424/61; 522/104, 107, 113, 114, 120, 121, 522/178, 182, 902; 523/137, 105, 300
See application file for complete search history.

(56) References Cited

U.S. PATENT DOCUMENTS

| 4,085,442 | A | * | 4/1978 | Liaukus et al. | 345/556 |
| 4,495,172 | A | * | 1/1985 | Orlowski et al. | 424/61 |
| 4,871,534 | A | * | 10/1989 | Montgomery | 424/61 |
| 5,127,414 | A | * | 7/1992 | Mast et al. | 132/73 |
| 6,060,073 | A | * | 5/2000 | Keller | 424/401 |

FOREIGN PATENT DOCUMENTS

JP   54-046240   *   4/1979

* cited by examiner

*Primary Examiner*—Sanza L McClendon
(74) *Attorney, Agent, or Firm*—Blakely Sokoloff Taylor & Zafman

(57) ABSTRACT

A method and kit for providing a tack-free artificial nail surface. The tack-free artificial nail surface may include an acrylic layer and a barrier layer. The acrylic layer may comprise an odorless monomer. The barrier layer may be of any material impervious to oxygen. The tack-free nail surface may be formed by application of the acrylic layer to a fingernail nail bed. The barrier layer may then be applied over the acrylic layer. The barrier layer blocks oxygen from the acrylic layer so that the acrylic layer may polymerize in the absence of oxygen.

27 Claims, 1 Drawing Sheet

METHOD OF OBTAINING A TACK-FREE ARTIFICIAL NAIL SURFACE USING ODORLESS MONOMERS

BACKGROUND

1. Field

A tack-free artificial nail surface formed using odorless monomers.

2. Background

Free Radical Polymerization is usually carried out in vacuum or inert atmosphere like argon or nitrogen. If carried out in atmosphere, oxygen present in air, acts as a radical scavenger and inhibits polymerization. The resulting polymer may or may not achieve the molecular weight to yield desired properties.

Some monomers like ethyl methacrylate ("EMA") or methyl methacrylate ("MMA") are exceptions because growing EMA radicals prefer reacting with another EMA monomer instead of reacting with oxygen or $k_{MM} \ggggg k_{MMO2}$ where k=rate of propagation of polymer, MM=reaction of growing polymer radical with another monomer and MO2=reaction of growing polymer radical with oxygen. The above equation reveals that the growing polymer radicals are very selective and almost exclusively react with another EMA monomer. Thus, in spite of EMA emitting a strong odor, this system is consistently used in the artificial nail industry.

In case of odorless monomers such as methoxyethoxy ethyl methacrylate ("MOEOEMA") and tetrahydrofurfuryl methacrylate ("THFMA"), the growing polymer radical is not very selective and it reacts with atmospheric oxygen almost as well as with another monomer. In this case the equation happens to be $k_{MM} > k_{MMO2}$. The growing polymer near the surface reacts with atmospheric oxygen resulting in a tacky surface. Thus, polymerization results in a high molecular weight polymer formed under a low molecular weight polymer, which is the tacky surface. The manicurist must then remove this tacky layer from the surface to reveal a hard plastic coating.

The resultant tacky layer is undesirable because the manicurist has to put a very thick coat on the nail bed for nail enhancement. The thickness of the finished product gives it a very plastic look and not the natural look of EMA. The manicurist also incorrectly assumes that the bottom layers are not fully cured. Thus, this tacky layer prevents these odorless systems from capturing a significant share of the artificial nail market.

Efforts have been made to eliminate the tacky layer. In other systems, adding wax to the system has helped eliminate the tacky surface. The wax rises to the surface and shields the growing polymer from oxygen and polymerization proceeds to completion. The wax then flakes off. For some unknown reason, the addition of wax to the system disclosed in the present application does not eliminate the tacky surface. Efforts to eliminate the tacky surface have also included carrying out polymerization in a nitrogen or argon atmosphere. Although this procedure has been successful, it is not a practical solution. A further option is immersion of the polymerizing nails in warm water (which excludes oxygen and speeds the cure). This once popular method is no longer considered good practice because it creates a substantial risk of skin sensitization due to traces of uncured monomer in the water. Significant positive attributes of these systems, like non-crystallizing and non-lifting phenomena, are overlooked in the face of this tackiness. Tackiness has become a big hurdle to commercial success of these odorless systems.

Thus, an odorless artificial nail system that results in a non-tacky nail surface remains desirable.

BRIEF DESCRIPTION OF THE DRAWINGS

Various embodiments are illustrated by way of example and not by way of limitation in the figures of the accompanying drawings in which like references indicate similar elements. It should be noted that different references to "an," "one," or "various" embodiments in this disclosure are not necessarily to the same embodiment, and such references mean at least one.

DETAILED DESCRIPTION

Figure 1:
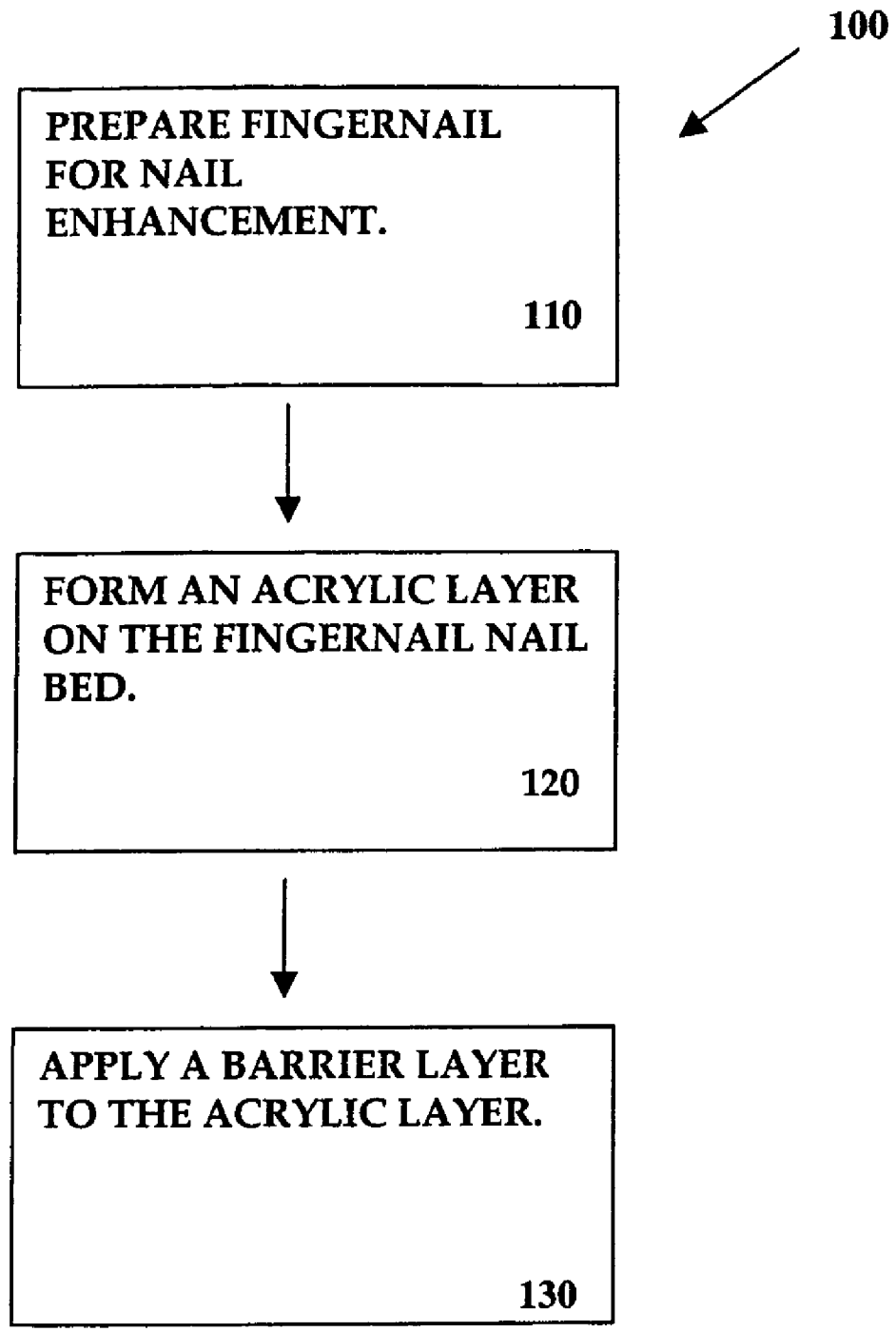
FIG. 1 is a flow chart of one embodiment for formation of a tack-free artificial nail surface.

FIG. 1 is an illustration of one embodiment of a method for forming a tack-free artificial nail surface. In one embodiment, the artificial nail may be made of an acrylic material. In another embodiment, the artificial nail may be made of any material capable of forming a hard plastic coating.

In one embodiment, the tack-free artificial nail may be formed by applying an acrylic layer and a barrier layer, or barrier coating, to a fingernail bed. The barrier layer may be applied over the acrylic layer. The barrier layer is impervious to atmospheric oxygen thereby allowing the acrylic layer to polymerize in the absence of atmospheric oxygen into a non-tacky nail surface. The acrylic layer may be made of a methacrylate monomer. The methacrylate monomer may be odorless. The monomer may be capable of polymerizing to form a durable plastic coating over the fingernail bed. The monomer may be a methoxyethoxy ethyl methacrylate or a tetrahydrofurfuryl methacrylate. The monomer may be in a liquid form. The acrylic layer, in the form of a plastic coating, may be made of a monomer/polymer mixture.

In one embodiment, the acrylic layer may be made of a mixture of the monomer in liquid form having a co-initiator and a polymer powder having an initiator. The co-initiator may include, but is not limited to, for example a dimethyl p-toluidine and a dihydroxyethyl p-toluidine. The initiator may be, but is not limited to, for example a benzoyl peroxide. The mixture may further include additives to prevent yellowing of the nail surface. For example, the additive may be selected from the group including, but not limited to, a sunscreen such as drometriazole (triazole family) and benzophenone. Additionally, the additive may be a blue dye such as Violet 2 and Violet 34.

In an alternative embodiment, the acrylic layer may be made of a mixture of a liquid monomer having an Ultra-violet (UV) light initiator (i.e., photoinitiator) and a polymer powder with or without benzoyl peroxide. The UV light initiator may include, but is not limited to, for example a hydroxymethylphenyl propanone and a phenyl phosphinate. The mixture may further include additives to prevent yellowing of the nail surface.

The barrier layer is any material impervious to oxygen. In one embodiment, a suitable barrier layer may be a cyanoacrylate glue. A suitable barrier layer may also include, but is not limited to, a urethane, an epoxy or an acrylic. The barrier layer may be formed by, for example, applying a coat of cyanoacrylate glue over the acrylic layer. The barrier layer experiences an anionic cure that is not inhibited by oxygen. Thus, providing a smooth, hard, non-tacky surface over the acrylic layer.

In one embodiment, the fingernail bed (i.e., nail bed) is prepared for nail enhancement (110). The nail bed may be prepared by cleaning and shaping the nail bed. Preparation of the nail bed may further include applying a fingernail dehydrator to the fingernail bed. The fingernail dehydrator may be, but is not limited to, for example a volatile solvent like ethyl acetate. A nail tip may be applied to the nail bed. Once the nail bed is prepared, a liquid/powder mixture such as the methacrylate monomer and polymer described above may be applied to the nail bed to form the acrylic layer (120). Where a nail tip is applied to the nail bed, the mixture may be applied to both the exposed nail bed and nail tip. The acrylic layer may be sculpted and shaped as desired. Once the manicurist is done sculpting the acrylic layer, the barrier layer may be applied over the acrylic layer (130). This method blocks oxygen and allows the monomers beneath the barrier layer to polymerize resulting in a higher molecular weight tack-free polymer. The barrier layer experiences an anionic cure that is not inhibited by oxygen. Thus, providing a smooth, hard, non-tacky surface over the acrylic layer. Other oxygen barrier coatings such as urethanes, epoxies and acrylics will be equally effective.

Polymerization of the acrylic layer may occur by one of an amine promoted decomposition of peroxide reaction and photopolymerization. For example, where the acrylic layer includes the liquid monomer with dimethyl p-toluidine and the polymer powder with benzoyl peroxide, the dimethyl p-toluidine in liquid monomer facilitates decomposition of the benzoyl peroxide in polymer powder to form benzoyloxy radicals which then polymerize the methacrylate monomer. In an alternative embodiment, where the acrylic layer includes a liquid monomer having a photoinitiator and a polymer powder, UVA light may be applied to decompose the photoinitiator to form radicals which will then start polymerization of the methacrylate monomer.

The following specific examples are set forth to illustrate the various methods for forming the non-tacky artificial nail.

Example I

In one embodiment, after preparing the fingernail for nail enhancement, the nail bed may be dehydrated by applying a nail dehydrator such as ethyl acetate. Once the nail bed is dehydrated, a coat of nail primer may be applied. The acrylic layer in the form of the liquid/powder (i.e., monomer/polymer) mixture is applied over the primer. The manicurist may sculpt the nail into a desirable shape. Once the nail is sculpted, cyanoacrylate glue may be applied to the sculpted nail. The cyanoacrylate glue must be applied before polymerization of the acrylic layer has progressed to a significant degree, i.e. usually within approximately thirty seconds of applying the liquid/powder mixture. The cyanoacrylate glue experiences an anionic cure over the acrylic layer to produce a smooth, hard, non-tacky surface. The shape of the sculpted nail may then be refined by filing. This method may be repeated on each nail.

Example II

In another embodiment, the fingernail may be prepared for nail enhancement. Once prepared, the nail bed may be dehydrated. Instead of primer, one can coat the nail bed with cyanoacrylate glue. The liquid/powder mixture may be applied on top of the cyanoacrylate glue to form the acrylic layer. The nail may then be sculpted to achieve the desired shape. As soon as sculpting is complete, i.e. before curing has progressed significantly, a barrier layer or coating (e.g., cyanoacrylate glue) may be applied to the sculpted nail. The shape of the sculpted nail may then be refined by filing. This process should be repeated on each nail.

Example III

In still another embodiment, the non-tacky artificial nail may be formed by a primer less technique. In this embodiment, the fingernail may be prepared for nail enhancement. The fingernail may be dehydrated and the liquid/powder mixture applied to the nail bed to form the acrylic layer. The barrier layer may then be formed by coating the nail bed with cyanoacrylate glue. The shape of the sculpted nail may then be refined by filing. This process should be repeated on each nail.

Example IV

In one embodiment, after preparing the fingernail for nail enhancement, the nail bed may be dehydrated. Once the nail bed is dehydrated, a coat of nail primer may be applied. The acrylic layer in the form of the liquid monomer having a UV light initiator and polymer powder with or without benzoyl peroxide is applied over the primer. The manicurist may sculpt the nail into a desirable shape. In this method, polymerization commences only when the nails are exposed to UVA light. Hence depending on the configuration of the lamp, all 5 or 10 nails may be sculpted before application of cyanoacrylate glue. The nail is then cured under a UVA light. The shape of the sculpted nail may then be refined by filing.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

What is claimed is:

1. A method comprising:
    applying an acrylic layer to a fingernail bed, the acrylic layer having an odorless methacrylate monomer that, when applied, polymerizes to form a durable plastic coating; and
    applying a barrier layer to the acrylic layer before polymerization of the acrylic layer is complete, the barrier layer being impervious to atmospheric oxygen allowing for polymerization of the acrylic layer in the absence of oxygen to yield a non-tacky surface; and
    curing and hardening the barrier layer.

2. The method of claim 1, wherein the methacrylate monomer comprises at least one of a methoxyethoxy ethyl methacrylate and a tetrahydrofurfuryl methacrylate.

3. The method of claim 1, wherein the barrier layer comprises a cyanoacrylate glue.

4. The method of claim 1, wherein the barrier layer is selected from a urethane, an epoxy and an acrylic.

5. The method of claim 1, wherein the acrylic layer further comprises an additive to prevent yellowing.

6. The method of claim 1, further comprising:
    a co-initiator, the co-initiator combined with the methacrylate monomer, the methacrylate monomer in liquid form; and
    a polymer powder, the polymer powder comprising an initiator such that the acrylic layer may be cured by an amine promoted decomposition of peroxide reaction.

7. The method of claim 1, further comprising:
    a photoinitiator, the photoinitiator combined with the methacrylate monomer in liquid form; and a polymer powder, the polymer powder comprising an initiator such that the acrylic layer may be cured under UVA light by a photopolymerization process.

8. A method comprising:

applying a cyanoacrylate glue to a fingernail bed;

applying an acrylic layer to the cyanoacrylate glue, the acrylic layer having an odorless methacrylate monomer capable of polymerizing to form a durable plastic coating; and applying a barrier layer to the acrylic layer before polymerization of the acrylic layer is complete, the barrier layer being impervious to atmospheric oxygen allowing for polymerization of the acrylic layer in the absence of oxygen to yield a non-tacky surface, provided that the barrier layer does not consist essentially of a wax.

9. The method of claim 8, wherein the methacrylate monomer comprises at least one of a methoxyethoxy ethyl methacrylate and a tetrahydrofurfuryl methacrylate.

10. The method of claim 8, wherein the cyanoacrylate glue is used instead of a primer.

11. The method of claim 8, wherein the barrier layer is applied over a final acrylic layer.

12. The method of claim 8, wherein the barrier layer is selected from a cyanoacrylate glue, a urethane, an epoxy and an acrylic.

13. A kit comprising:

an odorless methacrylate monomer with a co-initiator;

an additive to prevent yellowing;

a polymer powder with an initiator; and a barrier coating material impervious to oxygen, the barrier coating material to facilitate polymerization of the methacrylate monomer in the absence of atmospheric oxygen, wherein the barrier coating material cures and hardens when applied.

14. The kit of claim 13, wherein the methacrylate monomer comprises at least one of a methoxyethoxy ethyl methacrylate and a tetrahydrofurfuryl methacrylate.

15. The kit of claim 13, wherein the barrier coating material experiences an anionic cure uninhibited by oxygen when applied to the methacrylate monomer.

16. The kit of claim 13, wherein the barrier coating material is selected from a cyanoacrylate glue, a urethane, an epoxy and an acrylic.

17. The kit of claim 13, further comprising at least one of a fingernail primer and a fingernail dehydrator.

18. The kit of claim 13, wherein the initiator comprises a benzoyl peroxide.

19. A kit comprising:

an odorless methacrylate monomer with a photoinitiator;

an additive to prevent yellowing;

a polymer powder; and a barrier coating material impervious to oxygen, the barrier coating material to facilitate polymerization of the methacrylate monomer in the absence of atmospheric oxygen, provided that the barrier coating material does not consist essentially of a wax.

20. The kit of claim 19, wherein the methacrylate monomer comprises at least one of a methoxyethoxy ethyl methacrylate and a tetrahydrofurfuryl methacrylate.

21. The kit of claim 19, wherein the barrier coating material experiences an anionic cure uninhibited by oxygen when applied to the methacrylate monomer.

22. The kit of claim 19, wherein the barrier coating material is selected from a cyanoacrylate glue, a urethane, an epoxy and an acrylic.

23. The kit of claim 19, further comprising at least one of a fingernail primer and a fingernail dehydrator.

24. The kit of claim 19, wherein the photoinitiator comprises at least one of a hydroxymethylphenyl propanone and phenyl phosphinate.

25. The kit of claim 19, wherein the polymeric powder includes benzoyl peroxide.

26. A method comprising:

applying a first layer over a fingernail, wherein polymerization of the first layer is susceptible to atmospheric oxygen;

applying a barrier layer over the first layer before polymerization of the first layer is complete, the barrier layer to shield the first layer from the atmospheric oxygen;

curing the first layer; and curing the barrier layer by a cure that is not inhibited by oxygen.

27. The method of claim 26, wherein the first layer is cured by free radical polymerization and the barrier layer is cured through an anionic cure.

* * * * *

UNITED STATES PATENT AND TRADEMARK OFFICE
CERTIFICATE OF CORRECTION

PATENT NO. : 7,622,511 B1  Page 1 of 1
APPLICATION NO. : 11/217053
DATED : November 24, 2009
INVENTOR(S) : Sirdesai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1057 days.

Signed and Sealed this

Twenty-sixth Day of October, 2010

David J. Kappos
*Director of the United States Patent and Trademark Office*